|  US009279021B2

(12) United States Patent
Khabar

(10) Patent No.: US 9,279,021 B2
(45) Date of Patent: Mar. 8, 2016

(54) METHOD FOR INCREASING THE EXPRESSION AND/OR STABILITY OF A PROTEIN IN A CELL AND A PEPTIDE FOR USE IN SUCH METHOD

(71) Applicant: King Faisal Specialist Hospital and Research Centre, Riyadh (SA)

(72) Inventor: Khalid S. Abu Khabar, Riyadh (SA)

(73) Assignee: King Faisal Specialist Hospital & Research Centre, Riyadh (SA)

( * ) Notice: Subject to any disclaimer, the term of this patent is extended or adjusted under 35 U.S.C. 154(b) by 0 days.

(21) Appl. No.: 14/304,390

(22) Filed: Jun. 13, 2014

(65) Prior Publication Data

US 2014/0295544 A1    Oct. 2, 2014

Related U.S. Application Data

(63) Continuation of application No. 13/811,454, filed as application No. PCT/EP2010/004862 on Aug. 9, 2010, now Pat. No. 8,791,241.

(51) Int. Cl.
| A61K 49/00 | (2006.01) |
| C07K 16/44 | (2006.01) |
| C07K 14/435 | (2006.01) |
| C07K 14/00 | (2006.01) |

(52) U.S. Cl.
CPC ............... *C07K 16/44* (2013.01); *C07K 14/001* (2013.01); *C07K 14/435* (2013.01); *C07K 14/43595* (2013.01); *C07K 2319/60* (2013.01)

(58) Field of Classification Search
None
See application file for complete search history.

(56) References Cited

U.S. PATENT DOCUMENTS 8,791,241 B2 *    7/2014    Khabar .................... 530/350

OTHER PUBLICATIONS

Database Genbank [Online], "Synthetic construct 'ALL-ancestor' ancestral fluorescent protein variant," Nov. 2004, Database Accession No. AY648257.
Kao, Hung-Teh et al., "Dynamic Regulation of Fluorescent Proteins from a Single Species of Coral," *Marine Biotechnology*, Oct. 2007, 9(6):733-746.
Zacharias, David A., et al. "Molecular Biology and Mutation of Green Fluorescent Protein," *Green Fluorescent Protein: Properties, Applications, and Protocols*, 2006, 2nd ed., p. 83-118.

* cited by examiner

*Primary Examiner* — Marcela M Cordero Garcia
*Assistant Examiner* — Mindy Newman
(74) *Attorney, Agent, or Firm* — Saliwanchik, Lloyd & Eisenschenk

(57) ABSTRACT

The present invention relates to fluorescent proteins, in particular green fluorescent proteins (GFPs), with increased activity in cells, and thus increased signal strength. A further aspect of the present invention relates to the use of peptides for increasing the expression and/or stability of a protein in a cell.

9 Claims, 6 Drawing Sheets

SEQUENCE LISTING

<160> NUMBER OF SEQ ID NOS: 11

<210> SEQ ID NO 1

```
<211> LENGTH: 213
<212> TYPE: PRT
<213> ORGANISM: Artificial Sequence
<220> FEATURE:
<223> OTHER INFORMATION: consensus sequence of 6 different GFPs

<400> SEQUENCE: 1

Met Lys Ile Lys Leu Arg Met Glu Gly Ser Val Asn Gly His Lys Phe
1               5                   10                  15

Ser Ile Glu Gly Glu Gly Lys Gly Lys Pro Tyr Glu Gly Lys Gln Thr
            20                  25                  30

Met Asn Leu Lys Val Thr Lys Gly Gly Pro Leu Pro Phe Ser Phe Asp
        35                  40                  45

Ile Leu Ser Thr Val Phe Gln Tyr Gly Asn Arg Cys Phe Thr Lys Tyr
    50                  55                  60

Pro Asp Asp Ile Pro Asp Tyr Phe Lys Gln Ala Phe Pro Glu Gly Tyr
65                  70                  75                  80

Ser Trp Glu Arg Thr Met Thr Phe Glu Asp Gly Gly Ile Val Lys Val
                85                  90                  95

Ser Ser Asp Ile Ser Leu Glu Glu Asp Cys Phe Val Tyr Lys Ile Arg
            100                 105                 110

Phe Asp Gly Val Asn Phe Pro Ala Asn Gly Pro Val Met Gln Lys Lys
        115                 120                 125

Thr Leu Lys Trp Glu Pro Ser Thr Glu Lys Met Tyr Val Arg Asp Gly
    130                 135                 140

Val Leu Lys Gly Asp Val Lys Met Ala Leu Leu Leu Glu Gly Gly Gly
145                 150                 155                 160

His Tyr Arg Cys Asp Phe Lys Thr Thr Tyr Lys Ala Lys Lys Val Val
                165                 170                 175

Gln Leu Pro Asp Tyr His Ser Val Asp His Arg Ile Glu Ile Thr Ser
            180                 185                 190

His Asp Lys Asp Tyr Asn Lys Val Lys Leu Tyr Glu His Ala Val Ala
        195                 200                 205

His Val Ser Leu Leu
    210

<210> SEQ ID NO 2
<211> LENGTH: 219
<212> TYPE: PRT
<213> ORGANISM: Artificial Sequence
<220> FEATURE:
<223> OTHER INFORMATION: consensus sequence of 26 different GFPs
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
```

```
<222> LOCATION: (40)..(40)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid
<220> FEATURE:
<221> NAME/KEY: misc_feature
<222> LOCATION: (120)..(120)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (175)..(175)
<223> OTHER INFORMATION: Xaa can be any naturally occurring amino acid
<220> FEATURE:
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (198)..(199)
<223> OTHER INFORMATION: Xaa can be any naturally occurring amino acid
<220> FEATURE:
<221> NAME/KEY: misc_feature
<222> LOCATION: (201)..(201)
<223> OTHER INFORMATION: Xaa can be any naturally occurring amino acid
<220> FEATURE:
<221> NAME/KEY: misc_feature
<222> LOCATION: (218)..(218)
<223> OTHER INFORMATION: Xaa can be any naturally occurring amino acid

<400> SEQUENCE: 2

Met Xaa Val Ile Xaa Xaa Met Lys Ile Lys Leu Arg Met Glu Gly Xaa
 1               5                  10                  15

Val Asn Gly His Lys Phe Ser Ile Glu Gly Glu Gly Xaa Gly Xaa Pro
            20                  25                  30

Tyr Glu Gly Lys Gln Thr Met Xaa Leu Xaa Val Thr Lys Gly Gly Pro
        35                  40                  45

Leu Pro Phe Ser Phe Asp Ile Leu Ser Thr Val Phe Xaa Tyr Gly Asn
    50                  55                  60

Arg Xaa Phe Thr Lys Tyr Pro Asp Asp Ile Pro Asp Tyr Phe Lys Gln
65                  70                  75                  80
```

Ala Phe Pro Glu Gly Tyr Ser Trp Glu Arg Thr Met Xaa Phe Glu Asp
                85                  90                  95

Gly Gly Ile Val Xaa Val Ser Ser Asp Ile Ser Leu Glu Xaa Asp Cys
            100                 105                 110

Phe Val Tyr Lys Ile Arg Phe Xaa Gly Val Asn Phe Pro Ala Asn Gly
            115                 120                 125

Pro Val Met Gln Lys Lys Thr Leu Lys Trp Glu Pro Ser Xaa Glu Lys
130                 135                 140

Met Tyr Val Xaa Asp Gly Val Leu Lys Gly Asp Val Lys Met Ala Leu
145                 150                 155                 160

Leu Leu Glu Gly Gly His Tyr Arg Cys Asp Phe Lys Thr Xaa Tyr
                165                 170                 175

Lys Ala Xaa Lys Val Val Xaa Leu Pro Asp Tyr His Phe Val Asp His
            180                 185                 190

Arg Ile Glu Ile Thr Xaa Xaa Asp Xaa Asp Tyr Asn Lys Val Lys Leu
            195                 200                 205

Tyr Glu His Ala Val Ala His Val Ser Xaa Leu
210                 215

<210> SEQ ID NO 3
<211> LENGTH: 221
<212> TYPE: PRT
<213> ORGANISM: Artificial Sequence
<220> FEATURE:
<223> OTHER INFORMATION: combination of SEQ ID NO: 1 and SEQ ID NO: 2

<400> SEQUENCE: 3

Met Pro Val Ile Lys Pro Val Met Lys Ile Lys Leu Arg Met Glu Gly
1               5                   10                  15

Ser Val Asn Gly His Lys Phe Ser Ile Glu Gly Glu Gly Lys Gly Lys
            20                  25                  30

Pro Tyr Phe Gly Lys Gln Thr Met Asn Leu Arg Val Thr Lys Gly Ala
            35                  40                  45

Pro Leu Pro Phe Ala Phe Asp Ile Leu Ser Thr Ala Phe Gln Tyr Gly
50                  55                  60

Asn Arg Cys Phe Thr Lys Tyr Pro Asp Asp Ile Pro Asp Tyr Phe Lys
65                  70                  75                  80

Gln Ser Phe Pro Glu Gly Tyr Ser Trp Glu Arg Thr Met Thr Phe Glu
                85                  90                  95

Asp Gly Gly Ile Val Lys Ile Arg Ser Asp Ile Ser Leu Glu Glu Asp
            100                 105                 110

Cys Phe Val Tyr Lys Ile Glu Phe Lys Gly Val Asn Phe Pro Ala Asn
            115                 120                 125

Gly Pro Val Met Gln Lys Lys Thr Leu Gly Trp Glu Pro Ser Thr Glu
130                 135                 140

Lys Met Tyr Met Arg Asp Gly Val Leu Val Gly Asp Val Lys Met Ala
145                 150                 155                 160

Leu Leu Leu Glu Gly Gly Gly His Tyr Arg Cys His Phe Lys Thr Thr
                165                 170                 175

Tyr Lys Ala Lys Lys Val Val Gln Leu Pro Asp Tyr His Phe Val Asp
            180                 185                 190

His Arg Ile Glu Ile Thr Ser His Asp Lys Asp Tyr Asn Lys Val Lys
            195                 200                 205

Leu Tyr Glu His Ala Ile Ala His Leu Ser Thr Ile Gly
210                 215                 220

<210> SEQ ID NO 4
<211> LENGTH: 221
<212> TYPE: PRT
<213> ORGANISM: Artificial Sequence
<220> FEATURE:
<223> OTHER INFORMATION: SEQ ID NO: 3 with S58T, K158T and Q62C

<400> SEQUENCE: 4

```
Met Pro Val Ile Lys Pro Val Met Lys Ile Lys Leu Arg Met Glu Gly
1               5                   10                  15

Ser Val Asn Gly His Lys Phe Ser Ile Glu Gly Glu Gly Lys Gly Lys
            20                  25                  30

Pro Tyr Phe Gly Lys Gln Thr Met Asn Leu Arg Val Thr Lys Gly Ala
        35                  40                  45

Pro Leu Pro Phe Ala Phe Asp Ile Leu Thr Thr Ala Phe Cys Tyr Gly
    50                  55                  60

Asn Arg Cys Phe Thr Lys Tyr Pro Asp Asp Ile Pro Asp Tyr Phe Lys
65                  70                  75                  80

Gln Ser Phe Pro Glu Gly Tyr Ser Trp Glu Arg Thr Met Thr Phe Glu
                85                  90                  95

Asp Gly Gly Ile Val Lys Ile Arg Ser Asp Ile Ser Leu Glu Glu Asp
            100                 105                 110

Cys Phe Val Tyr Lys Ile Glu Phe Lys Gly Val Asn Phe Pro Ala Asn
        115                 120                 125

Gly Pro Val Met Gln Lys Lys Thr Leu Gly Trp Glu Pro Ser Thr Glu
    130                 135                 140

Lys Met Tyr Met Arg Asp Gly Val Leu Val Gly Asp Val Thr Met Ala
145                 150                 155                 160

Leu Leu Leu Glu Gly Gly Gly His Tyr Arg Cys His Phe Lys Thr Thr
                165                 170                 175

Tyr Lys Ala Lys Lys Val Val Gln Leu Pro Asp Tyr His Phe Val Asp
            180                 185                 190

His Arg Ile Glu Ile Thr Ser His Asp Lys Asp Tyr Asn Lys Val Lys
        195                 200                 205

Leu Tyr Glu His Ala Ile Ala His Leu Ser Thr Ile Gly
    210                 215                 220
```

<210> SEQ ID NO 5
<211> LENGTH: 23
<212> TYPE: PRT
<213> ORGANISM: Artificial Sequence
<220> FEATURE:
<223> OTHER INFORMATION: consensus sequence of PEST-containing amino acid fragments of highly unstable genes

<400> SEQUENCE: 5

```
Leu Pro Ser Val Asp Glu Glu Ser Pro Glu Asp Ser Pro Glu Ser Pro
1               5                   10                  15

Val Ser Glu Glu Gly Thr Asp
            20
```

<210> SEQ ID NO 6
<211> LENGTH: 33
<212> TYPE: PRT
<213> ORGANISM: Danio rerio

<400> SEQUENCE: 6

Arg Asp Val Pro Asp Ala Glu Thr Gln Glu Ser Ser Pro Leu Asn Pro

```
1               5                   10                  15
Ala Thr Ala Ile Ser His His Gly Leu Pro Asn Ser Ala Ala Leu Leu
            20                  25                  30

Asp

<210> SEQ ID NO 7
<211> LENGTH: 244
<212> TYPE: PRT
<213> ORGANISM: Artificial Sequence
<220> FEATURE:
<223> OTHER INFORMATION: fusion protein consisting of SEQ ID NO: 4 and
      SEQ ID NO: 5

<400> SEQUENCE: 7

Met Pro Val Ile Lys Pro Val Met Lys Ile Lys Leu Arg Met Glu Gly
1               5                   10                  15

Ser Val Asn Gly His Lys Phe Ser Ile Glu Gly Glu Gly Lys Gly Lys
            20                  25                  30

Pro Tyr Phe Gly Lys Gln Thr Met Asn Leu Arg Val Thr Lys Gly Ala
            35                  40                  45

Pro Leu Pro Phe Ala Phe Asp Ile Leu Thr Thr Ala Phe Cys Tyr Gly
        50                  55                  60

Asn Arg Cys Phe Thr Lys Tyr Pro Asp Asp Ile Pro Asp Tyr Phe Lys
65                  70                  75                  80

Gln Ser Phe Pro Glu Gly Tyr Ser Trp Glu Arg Thr Met Thr Phe Glu
                85                  90                  95

Asp Gly Gly Ile Val Lys Ile Arg Ser Asp Ile Ser Leu Glu Glu Asp
            100                 105                 110

Cys Phe Val Tyr Lys Ile Glu Phe Lys Gly Val Asn Phe Pro Ala Asn
        115                 120                 125

Gly Pro Val Met Gln Lys Lys Thr Leu Gly Trp Glu Pro Ser Thr Glu
    130                 135                 140

Lys Met Tyr Met Arg Asp Gly Val Leu Val Gly Asp Val Thr Met Ala
145                 150                 155                 160

Leu Leu Leu Glu Gly Gly Gly His Tyr Arg Cys His Phe Lys Thr Thr
                165                 170                 175

Tyr Lys Ala Lys Lys Val Val Gln Leu Pro Asp Tyr His Phe Val Asp
            180                 185                 190

His Arg Ile Glu Ile Thr Ser His Asp Lys Asp Tyr Asn Lys Val Lys
        195                 200                 205

Leu Tyr Glu His Ala Ile Ala His Leu Ser Thr Ile Gly Leu Pro Ser
    210                 215                 220

Val Asp Glu Glu Ser Pro Glu Asp Ser Pro Glu Ser Pro Val Ser Glu
225                 230                 235                 240

Glu Gly Thr Asp

<210> SEQ ID NO 8
<211> LENGTH: 254
<212> TYPE: PRT
<213> ORGANISM: Artificial Sequence
<220> FEATURE:
<223> OTHER INFORMATION: fusion protein consisting of SEQ ID NO: 4 and
      SEQ ID NO: 6

<400> SEQUENCE: 8

Met Pro Val Ile Lys Pro Val Met Lys Ile Lys Leu Arg Met Glu Gly
1               5                   10                  15
```

```
Ser Val Asn Gly His Lys Phe Ser Ile Glu Gly Glu Gly Gly Lys
            20                  25                  30

Pro Tyr Phe Gly Lys Gln Thr Met Asn Leu Arg Val Thr Lys Gly Ala
        35                  40                  45

Pro Leu Pro Phe Ala Phe Asp Ile Leu Thr Thr Ala Phe Cys Tyr Gly
50                      55                  60

Asn Arg Cys Phe Thr Lys Tyr Pro Asp Asp Ile Pro Asp Tyr Phe Lys
65                  70                  75                  80

Gln Ser Phe Pro Glu Gly Tyr Ser Trp Glu Arg Thr Met Thr Phe Glu
                    85                  90                  95

Asp Gly Gly Ile Val Lys Ile Arg Ser Asp Ile Ser Leu Glu Glu Asp
                100                 105                 110

Cys Phe Val Tyr Lys Ile Glu Phe Lys Gly Val Asn Phe Pro Ala Asn
            115                 120                 125

Gly Pro Val Met Gln Lys Lys Thr Leu Gly Trp Glu Pro Ser Thr Glu
130                 135                 140

Lys Met Tyr Met Arg Asp Gly Val Leu Val Gly Asp Val Thr Met Ala
145                 150                 155                 160

Leu Leu Leu Glu Gly Gly Gly His Tyr Arg Cys His Phe Lys Thr Thr
                165                 170                 175

Tyr Lys Ala Lys Lys Val Val Gln Leu Pro Asp Tyr His Phe Val Asp
            180                 185                 190

His Arg Ile Glu Ile Thr Ser His Asp Lys Asp Tyr Asn Lys Val Lys
            195                 200                 205

Leu Tyr Glu His Ala Ile Ala His Leu Ser Thr Ile Gly Arg Asp Val
210                 215                 220

Pro Asp Ala Glu Thr Gln Glu Ser Ser Pro Leu Asn Pro Ala Thr Ala
225                 230                 235                 240

Ile Ser His His Gly Leu Pro Asn Ser Ala Ala Leu Leu Asp
                245                 250

<210> SEQ ID NO 9
<211> LENGTH: 573
<212> TYPE: PRT
<213> ORGANISM: Artificial Sequence
<220> FEATURE:
<223> OTHER INFORMATION: fusion protein consisting of firefly luciferase
      and SEQ ID NO: 5

<400> SEQUENCE: 9

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
            115                 120                 125
```

```
Ser Lys Lys Gly Leu Gln Lys Ile Leu Asn Val Gln Lys Lys Leu Pro
    130                 135                 140
Ile Ile Gln Lys Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
            180                 185                 190
Ala Leu Ile Met Asn Ser Ser Gly Ser Thr Gly Leu Pro Lys Gly Val
        195                 200                 205
Ala Leu Pro His Arg Thr Ala Cys Val Arg Phe Ser His Ala Arg Asp
    210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
            260                 265                 270
Phe Leu Arg Ser Leu Gln Asp Tyr Lys Ile Gln Ser Ala Leu Leu Val
        275                 280                 285
Pro Thr Leu Phe Ser Phe Phe Ala Lys Ser Thr Leu Ile Asp Lys Tyr
    290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
            340                 345                 350
Pro Glu Gly Asp Asp Lys Pro Gly Ala Val Gly Lys Val Val Pro Phe
        355                 360                 365
Phe Glu Ala Lys Val Val Asp Leu Asp Thr Gly Lys Thr Leu Gly Val
    370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp Glu His Phe
            420                 425                 430
Phe Ile Val Asp Arg Leu Lys Ser Leu Ile Lys Tyr Lys Gly Tyr Gln
        435                 440                 445
Val Ala Pro Ala Glu Leu Glu Ser Ile Leu Leu Gln His Pro Asn Ile
    450                 455                 460
Phe Asp Ala Gly Val Ala Gly Leu Pro Asp Asp Asp Ala Gly Glu Leu
465                 470                 475                 480
Pro Ala Ala Val Val Val Leu Glu His Gly Lys Thr Met Thr Glu Lys
                485                 490                 495
Glu Ile Val Asp Tyr Val Ala Ser Gln Val Thr Thr Ala Lys Lys Leu
            500                 505                 510
Arg Gly Gly Val Val Phe Val Asp Glu Val Pro Lys Gly Leu Thr Gly
        515                 520                 525
Lys Leu Asp Ala Arg Lys Ile Arg Glu Ile Leu Ile Lys Ala Lys Lys
530                 535                 540
```

Gly Gly Lys Ile Ala Val Leu Pro Ser Val Asp Glu Ser Pro Glu
545                 550                 555                 560

Asp Ser Pro Glu Ser Pro Val Ser Glu Glu Gly Thr Asp
            565                 570

<210> SEQ ID NO 10
<211> LENGTH: 583
<212> TYPE: PRT
<213> ORGANISM: Artificial Sequence
<220> FEATURE:
<223> OTHER INFORMATION: fusion protein consisting of firefly luciferase
      and SEQ ID NO: 6

<400> SEQUENCE: 10

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

```
Arg Gln Gly Tyr Gly Leu Thr Glu Thr Thr Ser Ala Ile Leu Ile Thr
                340                 345                 350

Pro Glu Gly Asp Asp Lys Pro Gly Ala Val Gly Lys Val Pro Phe
            355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp His Phe
            420                 425                 430

Phe Ile Val Asp Arg Leu Lys Ser Leu Ile Lys Tyr Lys Gly Tyr Gln
    435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
            530                 535                 540

Gly Gly Lys Ile Ala Val Arg Asp Val Pro Asp Ala Glu Thr Gln Glu
545                 550                 555                 560

Ser Ser Pro Leu Asn Pro Ala Thr Ala Ile Ser His His Gly Leu Pro
                565                 570                 575

Asn Ser Ala Ala Leu Leu Asp
                580

<210> SEQ ID NO 11
<211> LENGTH: 239
<212> TYPE: PRT
<213> ORGANISM: Artificial Sequence
<220> FEATURE:
<223> OTHER INFORMATION: enhanced green fluorescent protein (EGFP)

<400> SEQUENCE: 11

Met Val Ser Lys Gly Glu Glu Leu Phe Thr Gly Val Val Pro Ile Leu
1                   5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110
```

-continued

```
Val Lys Phe Glu Gly Asp Thr Leu Val Asn Arg Ile Glu Leu Lys Gly
    115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

METHOD FOR INCREASING THE EXPRESSION AND/OR STABILITY OF A PROTEIN IN A CELL AND A PEPTIDE FOR USE IN SUCH METHOD

CROSS REFERENCE TO A RELATED APPLICATION

This Application is a Continuation Application of co-pending application Ser. No. 13/811,454, filed Apr. 11, 2013; which is a National Stage Application of International Application Number PCT/EP2010/004862, filed Aug. 9, 2010; all of which are incorporated herein by reference in their entirety.

The Sequence Listing for this application is labeled "Sequence-listing.txt" which was created on Apr. 10, 2013 and is 28 KB. The entire content of the sequence listing is incorporated herein by reference in its entirety.

BACKGROUND

The present invention relates to fluorescent proteins, in particular green fluorescent proteins (GFPs), with increased activity in cells, and thus increased signal strength. A further aspect of the present invention relates to the use of peptides for increasing the expression and/or stability of a protein in a cell.

Because of its easily detectable green fluorescence, green fluorescent protein (GFP) from the jellyfish *Aequorea victoria* has been widely used to study gene expression and protein localization. GFP fluorescence does not require a substrate or cofactor; hence, it is possible to use this reporter in a wide variety of applications and cells.

The green fluorescent protein (GFP) is a protein composed of 238 amino acids (26.9 kDa), which exhibits bright green fluorescence when exposed to blue light. Although many other marine organisms have similar green fluorescent proteins, GFP traditionally refers to the protein first isolated from *A. victoria*. The GFP from *A. victoria* has a major excitation peak at a wavelength of 395 nm and a minor one at 475 nm. Its emission peak is at 509 nm which is in the lower green portion of the visible spectrum.

GFP has a typical beta barrel structure, consisting of one β-sheet with alpha helices containing the chromophore running through the centre. Inward facing sidechains of the barrel induce specific cyclization reactions in the tripeptide Ser65-Tyr66-Gly67 that lead to chromophore formation. This process of post-translational modification is referred to as maturation. The hydrogen bonding network and electron stacking interactions with these sidechains influence the colour of wildtype GFP and its numerous derivatives. The tightly packed nature of the barrel excludes solvent molecules, protecting the chromophore fluorescence from quenching by water.

Due to the potential for widespread usage and the evolving needs of researchers, many different mutants of GFP have been engineered (Shaner et al., 2005). The first major improvement was a single point mutation (S65T) reported in 1995. This mutation dramatically improved the spectral characteristics of GFP, resulting in increased fluorescence, photostability and a shift of the major excitation peak to 488 nm with the peak emission kept at 509 nm. This matched the spectral characteristics of commonly available FITC filter sets, increasing the practicality of use by the general researcher. A 37° C. folding efficiency (F64L) point mutant yielding enhanced GFP (EGFP) was discovered in 1995 and facilitated the use of GFPs in mammalian cells. Superfolder GFP, based on a series of mutations that allow GFP to rapidly fold and mature even when fused to poorly folding peptides, was reported in 2006.

Many other mutations have been made, including colour mutants; in particular blue fluorescent protein, cyan fluorescent protein and yellow fluorescent protein derivatives. BFP derivatives contain the Y66H substitution. The critical mutation in cyan derivatives is the Y66W substitution, which causes the chromophore to form with an indole rather than phenol component. The red-shifted wavelength of the YFP derivatives is accomplished by the T203Y mutation and is due to π-electron stacking interactions between the substituted tyrosine residue and the chromophore.

Semirational mutagenesis of a number of residues led to pH-sensitive mutants known as pHluorins, and later superecliptic pHluorins. By exploiting the rapid change in pH upon synaptic vesicle fusion, pHluorins tagged to synaptobrevin have been used to visualize synaptic activity in neurons.

Redox sensitive versions of GFP (roGFP) were engineered by introduction of cysteines into the beta barrel structure. The redox state of the cysteines determines the fluorescent properties of roGFP.

BRIEF SUMMARY OF THE INVENTION

It was an object of the present invention to provide fluorescent proteins, in particular GFPs, with increased activity in cells, and thus increased signal strength.

This object of the present invention is solved by a fluorescent protein having an amino acid sequence which is at least 82%, preferably at least 85%, more preferably at least 90%, even more preferably at least 95%, even more preferably at least 96%, even more preferably at least 97%, even more preferably at least 98%, even more preferably at least 99%, most preferably 100% identical to SEQ ID NO: 3 or an amino acid sequence which is at least 82%, preferably at least 85%, more preferably at least 90%, even more preferably at least 95%, even more preferably at least 96%, even more preferably at least 97%, even more preferably at least 98%, even more preferably at least 99%, most preferably 100% identical to a sequence wherein one to four amino acid residues of SEQ ID NO: 3 are replaced by another amino acid residue, wherein the one to four amino acid residues are selected from the group of S58, F61, Q62 and K158.

DETAILED DESCRIPTION OF THE INVENTION

In one embodiment, the fluorescent protein is a green fluorescent protein (GFP). However, it is known to a person skilled in the art that by exchanging single amino acids, e.g. in the chromophore region, the color of a fluorescent protein can be changed, e.g. to yellow (YFP), cyan (CFP), blue (BFP) and red (RFP).

In one embodiment, the fluorescent protein has an activity which is increased as compared to the polypeptide having the amino acid sequence of SEQ ID NO: 11 (EGFP). Preferably, the increased activity results in an increased fluorescence intensity of cells containing the fluorescent protein, wherein, preferably, the fluorescence intensity is increased by at least the factor of 1.5, preferably at the least the factor of 2, more preferably at least the factor of 3, as compared to cells containing the polypeptide having the amino acid sequence of SEQ ID NO: 11.

The term "activity" as used herein is meant to refer to the activity of the fluorescent protein in a cell, which is preferably quantified by measuring the fluorescence intensity of cells containing the fluorescent protein. The activity of a fluorescent protein in a cell is dependent on its concentration in the cell and its actual fluorescence, wherein the concentration is dependent, e.g., on the expression level and/or the stability within the cell. Therefore, an "increased activity" of the fluorescent protein according to the present invention may be due to an increased expression and/or an increased stability in the cell (e.g. based on a decreased degradation rate), but also due to increased fluorescence of the protein itself. Without wishing to be bound to a certain theory, the inventor believes that the increased activity, and thus increased signal strength of the fluorescent proteins according to the present invention are largely based on their increased expression in cells.

In one embodiment, S58 is replaced with T.
In one embodiment, F61 is replaced with L.
In one embodiment, Q62 is replaced with C.
In one embodiment, K158 is replaced with T.

In one embodiment, the fluorescent protein has an amino acid sequence which is identical to SEQ ID NO: 4. Preferably, the fluorescent protein has an activity which is increased as compared to the polypeptide having the amino acid sequence of SEQ ID NO: 11 (EGFP). Preferably, the increased activity results in an increased fluorescence intensity of cells containing the fluorescent protein, wherein, preferably, the fluorescence intensity is increased by at least the factor of 2, preferably at the least the factor of 3, more preferably at least the factor of 4, as compared to cells containing the polypeptide having the amino acid sequence of SEQ ID NO: 11.

In one embodiment, the fluorescent protein further comprises at its N-terminus or its C-terminus, preferably at its C-terminus, a peptide having an amino acid sequence which is at least 90%, preferably at least 95%, most preferably 100% identical to SEQ ID NO: 5 or to SEQ ID NO: 6 or to a fragment of SEQ ID NO: 6, wherein the fragment comprises at least 25 consecutive amino acids.

Preferably, the fluorescent protein which further comprises the peptide at its N-terminus or its C-terminus, preferably at its C-terminus, has an intracellular half-life of more than 10 hours, preferably of more than 15 hours, more preferably of more than 20 hours.

The term "intracellular half-life" as used herein is meant to refer to the period of time in which half of the fluorescent signal from the fluorescent protein expressed in cells disappears and half remains.

The objects of the present invention are also solved by a nucleic acid molecule coding for a fluorescent protein as defined above.

The term "nucleic acid molecule" as used herein includes DNA, such as cDNA or genomic DNA, and RNA. In a preferred embodiment, the nucleic acid molecule is DNA.

In one embodiment, the number of RNase L cleavage sites (in particular UU and/or UA dinucleotides) is reduced in the nucleic acid molecule in order to increase the expression of the encoded protein in cells, particularly in eukaryotic cells (see PCT/EP2010/000271).

The objects of the present invention are also solved by an expression construct comprising a nucleic acid molecule as defined above.

The term "expression construct" as used herein is meant to refer to an expression active PCR product or an expression vector.

The term "expression active PCR product" as used herein is meant to refer to a PCR product that is generated by PCR amplification using two primers complementary to sequences flanking the DNA sequence of interest, such as a cDNA, an open reading frame, or a gene that is contained in an expression vector, wherein the resulting PCR product contains a promoter, the DNA sequence of interest, and a termination sequence, and allows the expression of the DNA of interest, when transfected to a host cell (see also: Al-Zoghaibi et al., 2007).

Preferably, the expression vector is a plasmid, cosmid, virus, bacteriophage or another vector used conventionally e.g. in genetic engineering.

The objects of the present invention are also solved by a fusion protein comprising a fluorescent protein as defined above.

The objects of the present invention are further solved by a cell or tissue comprising a fluorescent protein as defined above, a nucleic acid molecule as defined above, an expression construct as defined above or a fusion protein as defined above.

The term "cell" as used herein refers to any prokaryotic or eukaryotic cell, wherein eukaryotic cells are preferred. Prokaryotic cells include bacteria of the species *Escherichia, Streptomyces, Salmonella* or *Bacillus*. Suitable eukaryotic cells include yeasts, such as *Saccharomyces cerevisiae* or *Pichia pastoris*, insect cells, such as *Drosophila* S2 or *Spodoptera* Sf9 cells, and mammalian cells. Mammalian cells that could be used include human HeLa, HEK293, Huh-7, H9 and Jurkat cells, mouse NIH3T3 and C127 cells, COS 1, COS 7 and CV1, quail QCI-3 cells, mouse L cells, Bowes melanoma cells and Chinese hamster ovary (CHO) cells. Also within the scope of the present invention are primary mammalian cells or cell lines. Primary cells are cells which are directly obtained from an organism. Suitable primary cells are, for example, mouse embryonic fibroblasts (MEF), mouse primary hepatocytes, cardiomyocytes and neuronal cells as well as mouse muscle stem cells (satellite cells) and stable, immortalized cell lines derived thereof. Appropriate culture media and conditions for the above-described (host) cells are known in the art.

The term "tissue" as used herein refers to a cellular organizational level intermediate between cells and a complete organism. Hence, a tissue is an ensemble of cells, not necessarily identical, but from the same origin, that together carry out a specific function.

The objects of the present invention are also solved by a kit comprising at least one of a fluorescent protein as defined above, a nucleic acid molecule as defined above, an expression construct as defined above, a fusion protein as defined above or a cell as defined above.

The various components of the kit may be packaged in one or more containers such as one or more vials. The vials may, in addition to the components, comprise preservatives or buffers for storage.

Another aspect of the present invention relates to the use of a peptide having an amino acid sequence which is at least 90%, preferably at least 95%, most preferably 100% identical to SEQ ID NO: 5 or to SEQ ID NO: 6 or to a fragment of SEQ ID NO: 6, wherein the fragment comprises at least 25 consecutive amino acids, for increasing the expression and/or stability of a protein, in particular a recombinant protein, in a cell.

In one embodiment, the peptide is fused to the N-terminus or the C-terminus of the protein. Preferably, the peptide is fused to the C-terminus of the protein.

In one embodiment the peptide is further used as a tag, preferably for antibody recognition ("epitope tag") and/or purification ("affinity tag") of the protein. Just as commonly used tags (e.g. myc, HA, His), the peptide may be removed by enzymatic cleavage, if a cleavage site, e.g., a specific protease site, is inserted between the peptide and the protein.

In one embodiment, the protein is a reporter protein.

The term "reporter protein" as used herein refers to fluorescent and non-fluorescent reporter proteins including (without being limited to) green fluorescent proteins (GFP), red fluorescence proteins (RFP), yellow fluorescent proteins (YFP), blue and cyan fluorescent proteins (CFP), luciferase, secreted alkaline phosphatase (SEAP), chloramphenicol acetyltransferase (CAT), secreted hormone, secreted cytokine, β-galactosidase, and other fluorescent and bioluminescent proteins.

Another aspect of the present invention relates to a peptide having an amino acid sequence which is at least 90%, preferably at least 95%, most preferably 100% identical to SEQ ID NO: 5.

A further aspect of the present invention relates to a fusion protein comprising a protein to be expressed in a cell and a peptide having an amino acid sequence which is at least 90%, preferably at least 95%, most preferably 100% identical to SEQ ID NO: 5 or to SEQ ID NO: 6 or to a fragment of SEQ ID NO: 6, wherein the fragment comprises at least 25 consecutive amino acids, wherein the peptide is fused to the N-terminus or the C-terminus of the protein to be expressed in a cell. Preferably, the peptide is fused to the C-terminus of the protein to be expressed in a cell.

In one embodiment, the protein to be expressed in a cell is a reporter protein as defined above.

Preferably, the fusion protein has an intracellular half-life which is increased by at least the factor of 1.5, preferably at the least the factor of 2, more preferably at least the factor of 3, as compared to the protein expressed to be in a cell without the peptide at its N-terminus or C-terminus.

In the case of non-fluorescent proteins, the term "intracellular half-life" simply refers to the period of time in which half of the initial amount of the non-fluorescent protein expressed in cells disappears, e.g. due to degradation, and half remains.

A still further aspect of the present invention relates to a nucleic acid molecule coding for a peptide as defined above or for a fusion protein as defined above.

In a further aspect, the present invention relates to a method of increasing the expression and/or stability of a protein, in particular a recombinant protein, to be expressed in a cell, which method comprises the steps of
    providing a nucleic acid molecule coding for a fusion protein as defined above;
    inserting (i.e. cloning) the nucleic acid molecule into an expression vector; and
    transforming, transfecting or injecting the expression vector into a cell.

In a further aspect, the present invention relates to a method of increasing the expression and/or stability of a protein, in particular a recombinant protein, to be expressed in a cell, which method comprises the steps of
    providing an expression active PCR product comprising a nucleic acid molecule coding for a fusion protein as defined above; and
    transfecting or injecting the expression active PCR product into a cell.

A further aspect of the present invention relates to an expression construct comprising a multiple cloning site followed or preceded by a nucleic acid molecule coding for a peptide having an amino acid sequence which is at least 90%, preferably at least 95%, most preferably 100% identical to SEQ ID NO: 5 or to SEQ ID NO: 6 or to a fragment of SEQ ID NO: 6, wherein the fragment comprises at least consecutive 25 amino acids.

In a further aspect, the present invention relates to a method of increasing the expression and/or stability of a protein, in particular a recombinant protein, to be expressed in a cell, which method comprises the steps of
    providing a nucleic acid molecule coding for the protein to be expressed in a cell;
    inserting (i.e. cloning) the nucleic acid molecule into an expression construct as defined above; and
    transforming, transfecting or injecting the expression construct into a cell.

A further aspect of the present invention relates to an antibody against a peptide having an amino acid sequence which is at least 90%, preferably at least 95%, most preferably 100% identical to SEQ ID NO: 5 or to SEQ ID NO: 6 or to a fragment of SEQ ID NO: 6, wherein the fragment comprises at least consecutive 25 amino acids.

The term "antibody" refers to a polypeptide having affinity for a target, antigen or epitope (here: a peptide or part of a peptide as defined above) and includes both naturally-occurring and engineered antibodies. The term "antibody" encompasses polyclonal, monoclonal, human, chimeric, humanized, primatized, veneered, and single chain antibodies, as well as fragments of antibodies (e.g., Fv, Fc, Fd, Fab, Fab', F(ab'), scFv, scFab, dAb).

A further aspect of the present invention relates to a cell comprising a peptide as defined above, a fusion protein as defined above, a nucleic acid molecule as defined above or an antibody as defined above.

A further aspect of the present invention relates to a kit comprising at least one of a peptide as defined above, a fusion protein as defined above, a nucleic acid molecule as defined above, an expression construct as defined above, an antibody as defined above or a cell as defined above.

The various components of the kit may be packaged in one or more containers such as one or more vials. The vials may, in addition to the components, comprise preservatives or buffers for storage.

As used herein, the term "percent (%) identical" refers to sequence identity between two amino acid sequences. Identity can be determined by comparing a position in both sequences, which may be aligned for the purpose of comparison. When an equivalent position in the compared sequences is occupied by the same amino acid, the molecules are considered to be identical at that position.

Preferably, non-identity (e.g. at most 18%, at most 15%, at most 10%, at most 5%, at most 4%, at most 3%, at most 2% or at most 1%) is based on amino acid exchanges which do not alter the activity or function of the fluorescent protein or peptide as compared to the fluorescent protein having the amino acid sequence of SEQ ID NO: 3 or a sequence wherein one to four amino acid residues of SEQ ID NO: 3 are replaced by another amino acid residue, wherein the one to four amino acid residues are selected from the group of S58, F61, Q62 and K158, or as compared to the peptide having the amino acid sequence of SEQ ID NO: 5 or SEQ ID NO: 6 or a fragment of SEQ ID NO: 6, wherein the fragment comprises at least 25 consecutive amino acids.

Generally, a person skilled in the art is aware of the fact that some amino acid exchanges in the amino acid sequence of a protein or peptide do not have any influence on the function, activity and/or (secondary or tertiary) structure of the protein or peptide at all. Amino acid sequences with such "neutral" amino acid exchanges as compared to the amino acid sequences disclosed herein fall within the scope of the present invention.

The fluorescent proteins according to the present invention show increased activity, and thus increased signal strength in cells. The fluorescent proteins according to the present invention are useful in a wide variety of applications, including the monitoring of gene expression and protein localization.

Furthermore, the inventor has surprisingly found that by fusing a peptide having an amino acid sequence which is at least 90%, preferably at least 95%, most preferably 100% identical to SEQ ID NO: 5 or to SEQ ID NO: 6 or to a fragment of SEQ ID NO: 6, wherein the fragment comprises at least 25 consecutive amino acids, to the N- or C-terminus of fluorescent proteins according to the present invention, their expression and/or stability, and thus their activity in cells is significantly increased. However, this principle is not restricted to the fluorescent proteins of the present invention, but can be used for any other reporter protein or, as a matter of fact, for any other protein to be expressed in a cell. It is especially useful for recombinant proteins, in particular for those, which are regularly hard to express in cells.

BRIEF DESCRIPTION OF THE SEQUENCE LISTING

Figure 1:
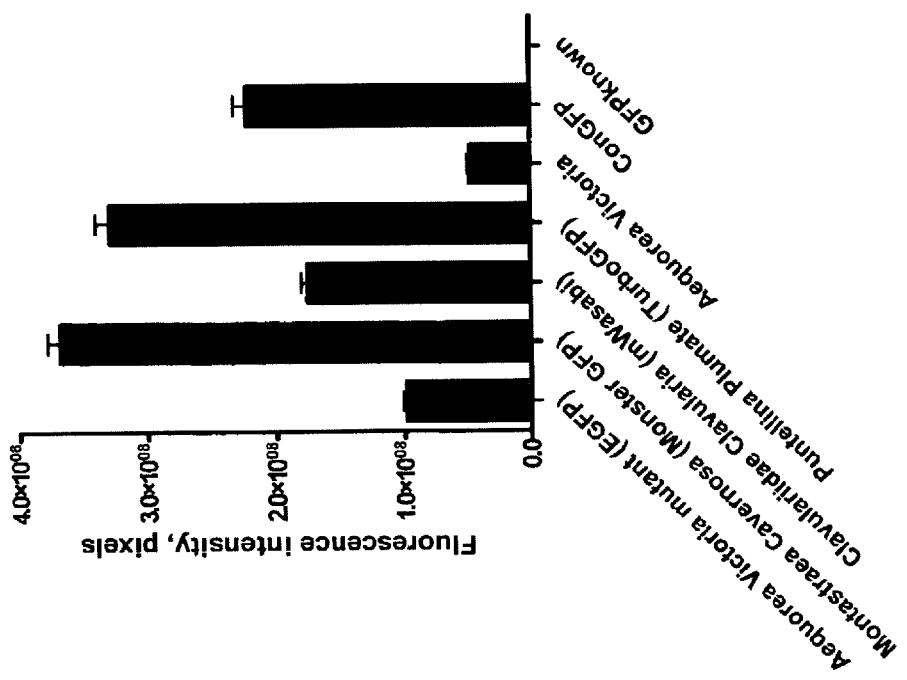
FIG. 1 shows the fluorescence intensity of Huh-7 cells two days after transfection with 75 ng of expression plasmids harboring different green fluorescent proteins (GFPs). Fluorescence was assessed from images captured by BD automated Bioimager and quantified using ProXcell algorithm. The values are Mean+/−SEM from four different wells.

SEQ ID NO: 1 is also referred to as GFPknown and is the consensus amino acid sequence based on an alignment of six GFPs known to have very good signal strength.

SEQ ID NO: 2 is the consensus amino acid sequence based on an alignment of 26 publicly available GenBank records of various GFPs.

SEQ ID NO: 3 is also referred to as conGFP and is a combination of SEQ ID NO: 1 and SEQ ID NO: 2. More specifically, SEQ ID NO: 1 was used to fill in the gaps (Xaa) in SEQ ID NO: 2.

SEQ ID NO: 4 is also referred to as conGFP-SKQ and is the amino acid sequence of conGFP (SEQ ID NO: 3) with the mutations S58T, K158T and Q62C.

SEQ ID NO: 5 is the amino acid sequence of 23-residue artificial peptide 1.

SEQ ID NO: 6 is the amino acid sequence of 33-residue peptide 2, which is derived from *Danio rerio* neuronal adhesion molecule L12.

SEQ ID NO: 7 is the amino acid sequence of a fusion protein consisting of conGFP-SKQ (SEQ ID NO: 4) and peptide 1 (SEQ ID NO: 5).

SEQ ID NO: 8 is the amino acid sequence of a fusion protein consisting of conGFP-SKQ (SEQ ID NO: 4) and peptide 2 (SEQ ID NO: 6).

SEQ ID NO: 9 is the amino acid sequence of a fusion protein consisting of firefly luciferase and peptide 1 (SEQ ID NO: 5).

SEQ ID NO: 10 is the amino acid sequence of a fusion protein consisting of firefly luciferase and peptide 2 (SEQ ID NO: 6).

SEQ ID NO: 11 is the amino acid sequence of *A. victoria* enhanced GFP (EGFP).

EXAMPLES

1. Materials & Methods 1.1 Plasmids

The coding regions of putative GPFs and their variants were first optimized using UU/UA dinucleotide frequency reduction approach as previously described (PCT/EP2010/000271), then submitted for custom gene synthesis. The coding regions were subcloned into an expression vector under the control of CMV promoter by using SalI and BamHI restriction.

1.2 Cell Lines

HEK293 cell line was obtained from American Type Culture Collection (ATCC; Rockville, Md.) and cultured in DMEM medium (Invitrogen, Carlsbad, Calif.) supplemented with 10% FBS and antibiotics. Huh-7 cell line was also propagated in DMEM medium with 10% FBS and antibiotics.

1.3 Reporter Transfection and Reporter Activity Assessment

Cells in 96-well clear bottom black microplates were transfected with 50-100 ng of the reporter vectors using lipofectamine 2000 reagent (Invitrogen). All transfections were performed in several replicates as indicated in the figure legends. The variance in GFP fluorescence among replicate microwells was <6%; thus, with this minimum variance, experiments do not warrant transfection normalization (Al-Zoghaibi et al., 2007). Automated laser-focus image capturing was performed using the high-throughput BD Pathway 435 imager (BD Biosciences, San Jose, Calif.). A wavelength of 482 nm was used for excitation. Image processing, segmentation, and fluorescence quantification was facilitated by ProXcell program and was previously described (al-Haj et al., 2009). Data are presented as mean values±standard error (SEM) of total fluorescence intensity in each well with replicate readings ranging from three to four as indicated in the text. Student's t-test was used when comparing two data groups while analysis of variance (ANOVA) was performed for each data set having three or more data groups.

2. Results

By alignment of the amino acid sequences of six different GFPs (from the organisms *Aequorea victoria, Pontellina plumata, Pitlosarcus, Montastrea cavernosa, Renilla mullerei, Clavulariidae clavularia*), which are known to have very good signal strength, a consensus amino acid sequence GFPknown (SEQ ID NO: 1) was obtained. Cells transfected with a plasmid harboring chemically synthesized DNA coding for the protein of SEQ ID NO: 1 showed no fluorescence (see FIG. 1).

An alignment of 26 publicly available GenBank records of various GFPs resulted in another consensus amino acid sequence (SEQ ID NO: 2), which, after transfection of cells with its chemically synthesized DNA, showed very poor fluorescence (data not shown).

The consensus sequence GFPknown (SEQ ID NO: 1) was used to fill in the gaps (denoted as Xaa) in SEQ ID NO: 2. The combination of SEQ ID NO:1 and SEQ ID NO: 2 resulted in conGFP (SEQ ID NO: 3). A BLAST search with the amino acid sequence of conGFP only revealed a few hits with less than 82% sequence identity, which included wildtype and artificial GFPs.

Cells transfected with conGFP-DNA showed lower fluorescence intensity than some individual wildtype GFPs (*Montastrea cavernosa, Puntellina plumate*), but it was significantly (i.e. at least 2-fold) higher than those of *A. victoria* GFPs, including EGFP (FIG. 1).

Figure 2:
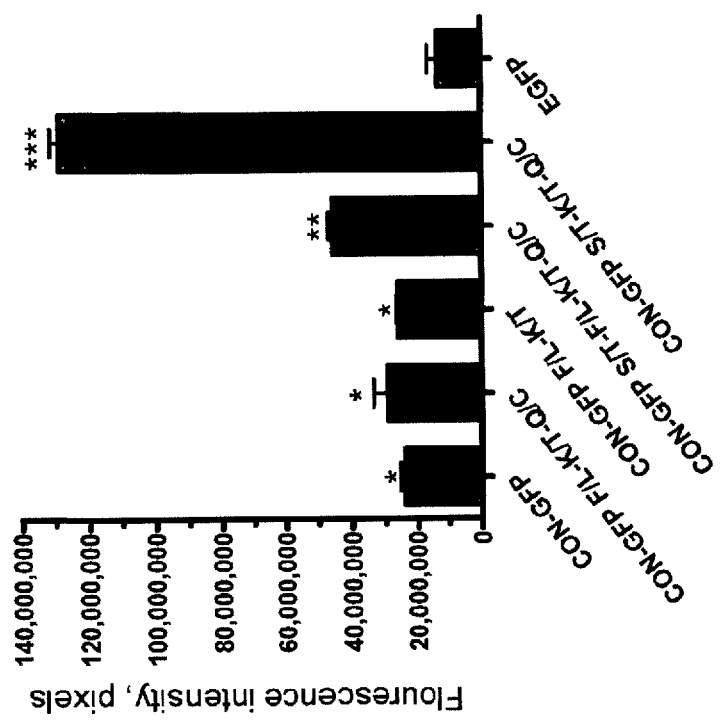
FIG. 2 shows the fluorescence intensity of HEK293 cells one day after transfection with 75 ng of PCR products derived from expression plasmids harboring EGFP, conGFP or various conGFP mutants. Fluorescence was assessed from images captured by BD automated Bioimager and quantified using ProXcell algorithm. The values represent Mean+/−SEM from four different wells. *,  and * denote <0.01, <0.005 and <0.001, respectively.

Next, DNA coding for several mutants of conGFP was synthesized and tested in HEK293 cells. The mutants included S58T, F61L, Q62C and K158T. Combinations of these mutants resulted in further increased fluorescence intensity, which was in all cases higher than that of EGFP (see FIG. 2). The triple mutant conGFP S58T K158T Q62C (also referred to as conGFP-SKQ, SEQ ID NO: 4) represented the best fluorescent protein with a fluorescence intensity which was about 5× higher than that of conGFP and about 10× higher than that of EGFP.

The performance of fluorescent proteins according to the present invention was further improved by adding peptide 1 (SEQ ID NO: 5), peptide 2 (SEQ ID NO: 6) or a fragment of peptide 2 with at least 25 consecutive amino acids to the N-terminus or the C-terminus of the proteins, more particular, a DNA sequence coding for one of these peptides was added in frame to the 5'-end or the 3'-end of the DNA coding for the fluorescent proteins.

Peptide 1 represents a consensus sequence of PEST-containing amino acid fragments of highly unstable genes. A PEST sequence is a peptide sequence which is rich in proline (P), glutamic acid (E), serine (S), and threonine (T). This sequence is associated with proteins that have a short intracellular half-life; hence, it is hypothesized that the PEST sequence acts as a signal peptide for protein degradation. Surprisingly, the addition of peptide 1 to the C-terminus of conGFP-SKQ (conGFP-SKQ-1) resulted in a dramatically increased fluorescence intensity of Huh-7 cells containing this fluorescent protein (see FIG. 3).

Figure 3:
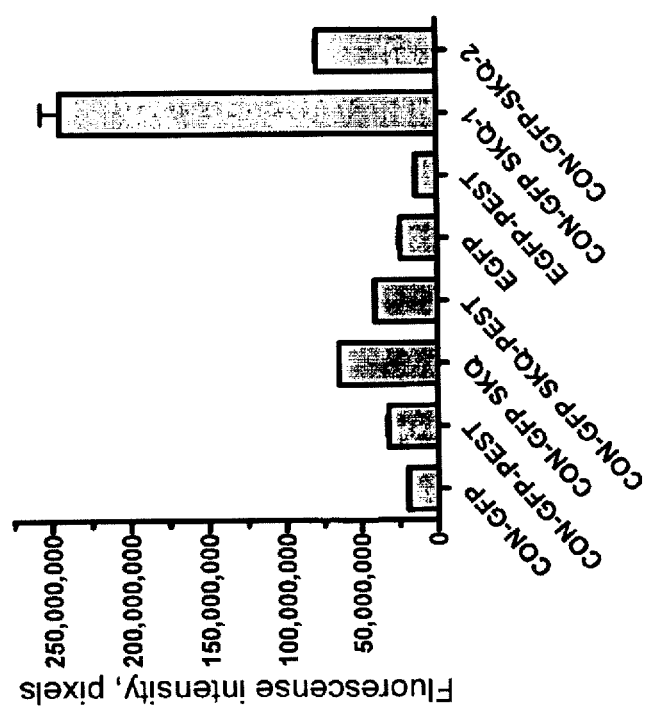
FIG. 3 shows the fluorescence intensity of Huh-7 cells one day after transfection with 50 ng of expression plasmids harboring various GFP variants with or without different peptides fused to their C-termini. "PEST" refers to the destabilization domain of the murine MODC1 gene. Fluorescence was assessed from images captured by BD automated Bioimager and quantified using ProXcell algorithm. The values represent Mean+/−SEM from four different wells.

Similarly, the addition of peptide 2, which is derived from the *Danio rerio* (zebrafish) neuronal adhesion molecule L12 and comprises a PEST-like domain, to the C-terminus of conGFP-SKQ (conGFP-SKQ-2) lead to a significantly increased fluorescence intensity (FIG. 3).

Figure 4:
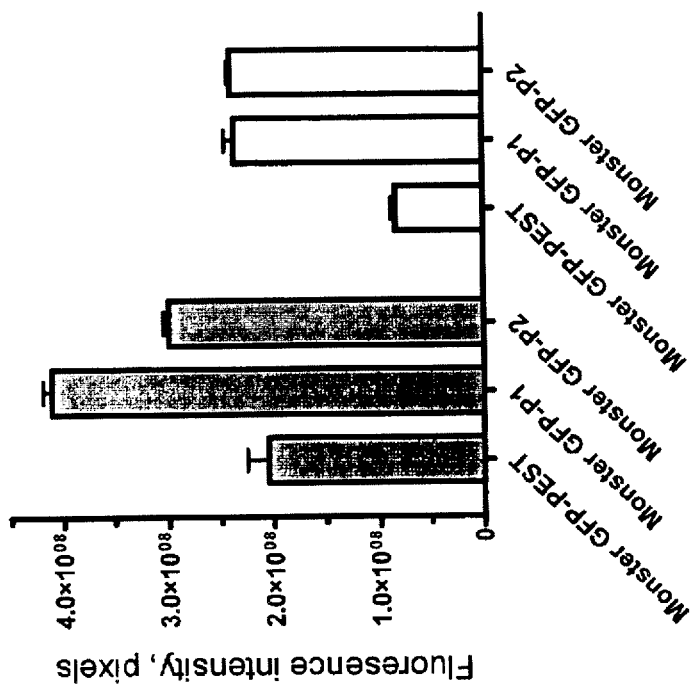
FIG. 4 shows the fluorescence intensity of Huh-7 cells two days after transfection with 50 ng of expression plasmids (grey columns) or 75 ng of PCR products (white columns) harboring various GFP variants with different peptides fused to their C-termini. Fluorescence was assessed from images captured by BD automated Bioimager and quantified using ProXcell algorithm. The values represent Mean+/−SEM from four different wells.

The effects observed when peptide 1 or 2 are added to the N-terminus or the C-terminus of fluorescent proteins according to the present invention are not limited to these specific proteins. As shown in FIG. 4, the fusion of the peptides to commercially available GFP ("Monster GFP") also increased the fluorescence intensity as compared to Huh-7 cells containing "wildtype" Monster GFP.

Figure 5:
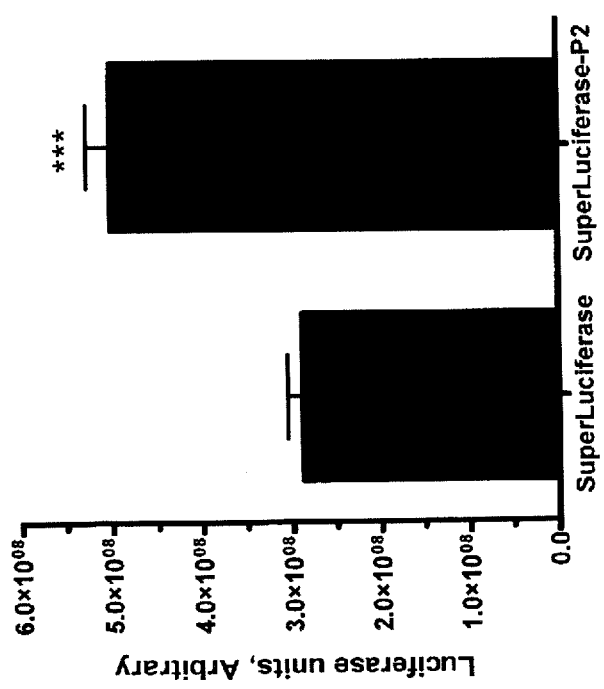
FIG. 5 shows luciferase activity in Huh-7 cells two days after transfection with 50 ng of expression plasmids harboring firefly luciferase cDNA or DNA coding for a fusion protein consisting of firefly luciferase and peptide 2 (SEQ ID NO: 10). Luciferase activity was measured in a 96-well standard luminometer. The values represent Mean+/−SEM from four different wells.

Moreover, the peptides (here: peptide 2) increased the activity of firefly luciferase in Huh-7 cells (FIG. 5).

Figure 6:
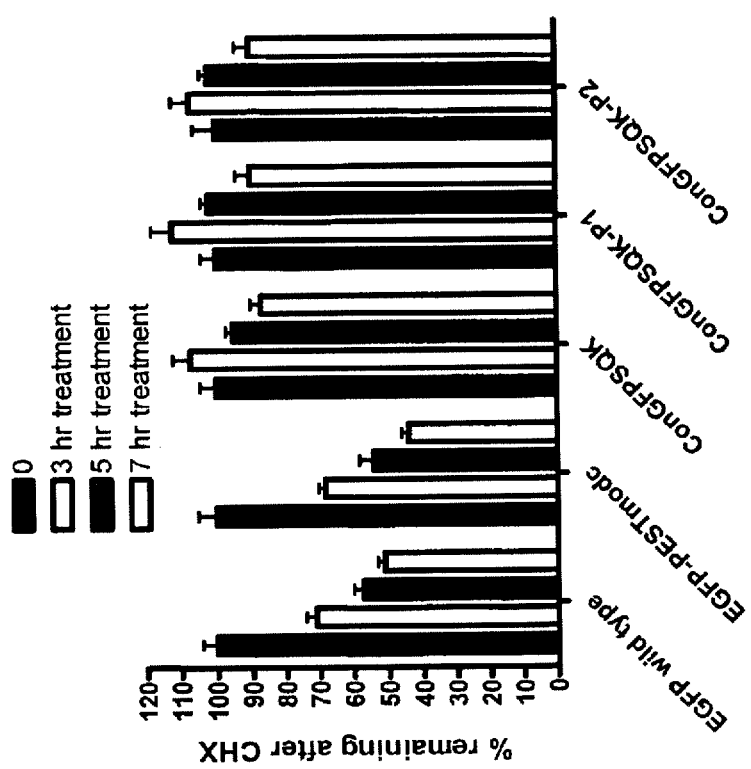
FIG. 6 shows the fluorescence intensity of Huh-7 cells one day after transfection with plasmids harboring various GFP variants and 3, 5, and 7 hours after subsequent treatment with cycloheximide (CHX). Fluorescence was assessed from images captured by BD automated Bioimager and quantified using ProXcell algorithm. The values represent Mean+/−SEM from four different wells.

In order to determine the intracellular stability of various GFP variants, Huh-7 cells were transfected with plasmids expressing "wildtype" EGFP, EGFP with the murine MODC1 PEST domain fused to its C-terminus (EGFP-PESTmodc), conGFP-SKQ, conGFP-SKQ-P1 and conGFP-SKQ-P2 (see FIG. 6). After 24 hours cells were treated with the protein synthesis inhibitor cycloheximide (CHX). Because of the non-specific toxicity of CHX experiments could not be extended to more than 6-8 hours. Both EGFP and EGFP-PESTmodc decayed at a significant rate. After 7 hours, there were only 51% (EGFP) and 44% (EGFP-PESTmodc) of the fluorescence activity remaining. Thus, the estimated intracellular half-life of the proteins was between three and four hours. In the case of conGFP-SQK, 87% of the fluorescence activity was remaining after 7 hours, while conGFP-SQK-P1 and -P2 (i.e. fusion proteins comprising conGFP-SQK and peptide 1 or 2 according to the present invention) were even more stable, with approximately 90% remaining after 7 hours. The half-life of conGFP-SQK appears to be more than 10 hours, more likely more than 20 hours, and the half-life of conGFP-SQK-P1 and -P2 is clearly more than 20 hours, possibly more than 24 hours. Thus, although peptides 1 and 2 of the present invention contain a PEST motif, there are no destabilization effects observed (in contrast to the murine MODC1 PEST domain; see FIG. 6).

Surprisingly, the peptides according to the present invention appear to increase the expression and/or intracellular stability of the proteins to which they are fused. An increased intracellular stability (or intracellular half-life) may be based on a decreased degradation rate of the fusion proteins.

REFERENCES

Al-Haj, L., Al-Ahmadi, W. Al-Saif, M. Demirkaya, O., and K. S. A. Khabar. 2009. Cloning-Free Regulated Monitoring of Reporter and Gene Expression. *BMC Molecular Biology* 10:20.

Al-Zoghaibi, F., T. Ashour, W. Al-Ahmadi, H. Abulleef, O. Demirkaya, and K. S. A. Khabar. 2007. Bioinformatics and experimental derivation of an efficient hybrid 3' untranslated region and use in expression active linear DNA with minimum poly(A) regions. *Gene* 391: 130-139.

Shaner, N., Steinbach, P., Tsien, R. 2005. A guide to choosing fluorescent proteins. *Nat Methods* 2 (12): 905-9.

I claim:

1. A method for increasing the expression and/or stability of a protein in a cell wherein said method comprises the use of a peptide having an amino acid sequence that is at least 90% identical to SEQ ID NO: 5 or to SEQ ID NO: 6 or to a fragment of SEQ ID NO: 6, wherein the fragment comprises at least 25 consecutive amino acids, wherein the peptide is fused to the N-terminus or the C-terminus of the protein to be expressed, and wherein said method comprises the steps of:
providing a nucleic acid molecule encoding a fusion protein of a peptide and a protein to be expressed, said peptide having an amino acid sequence that is at least 90% identical to SEQ ID NO: 5 or to SEQ ID NO: 6 or to a fragment of SEQ ID NO: 6, wherein the fragment comprises at least 25 consecutive amino acids and wherein the peptide is fused to the N-terminus or the C-terminus of the protein to be expressed in a cell;
inserting the nucleic acid molecule into an expression vector; and
transforming, transfecting or injecting the expression vector into a cell;
or wherein said method comprises the steps of:
providing an expression active PCR-product comprising a nucleic acid molecule encoding a fusion protein of a peptide and a protein to be expressed in a cell, said peptide having an amino acid sequence that is at least 90% identical to SEQ ID NO: 5 or to SEQ ID: 6 or to a fragment of SEQ ID NO: 6, wherein the fragment comprises at least 25 consecutive amino acids, and wherein the peptide is fused to the N-terminus or the C-terminus of the protein, and
transfecting or injecting the expression active PCR-product into a cell.

2. The method according to claim 1, wherein the peptide is further used as a tag for antibody recognition and/or purification of the protein.

3. The method according to claim 1, wherein the protein is a reporter protein.

4. A peptide having an amino acid sequence that is at least 90% identical to SEQ ID NO: 5.

5. A fusion protein comprising a protein to be expressed in a cell and a peptide having an amino acid sequence that is at least 90%-identical to SEQ ID NO: 5 or to SEQ ID NO: 6 or to a fragment of SEQ ID NO: 6, wherein the fragment comprises at least 25 consecutive amino acids, and wherein the peptide is fused to the N-terminus or the C-terminus of the protein to be expressed in a cell.

6. The fusion protein according to claim 5, wherein the protein to be expressed in a cell is a reporter protein.

7. A nucleic acid molecule encoding a peptide having an amino acid sequence that is at least 90% identical to SEQ ID NO:5 or for a fusion protein according to claim 5, wherein the nucleic acid molecule is cDNA.

8. An expression construct comprising a multiple cloning site followed or preceded by a nucleic acid molecule encoding a peptide having an amino acid sequence that is at least 90%-identical to SEQ ID NO: 5 or to SEQ ID NO: 6 or to a fragment of SEQ ID NO: 6, wherein the fragment comprises at least 25 consecutive amino acids, and wherein the nucleic acid molecule is cDNA.

9. A kit comprising at least one of a peptide having an amino acid sequence that is at least 90% identical to SEQ ID NO: 5; a fusion protein according to claim 5; a nucleic acid molecule encoding a peptide having an amino acid sequence that is at least 90% identical to SEQ ID NO:5 or a fusion protein according to claim 5; or a cell comprising a peptide having an amino acid sequence that is at least 90% identical to SEQ ID NO: 5, a fusion protein according to claim 5, a nucleic acid molecule encoding a peptide having an amino acid sequence that is at least 90% identical to SEQ ID NO:5 or for a fusion protein according to claim 5, wherein the nucleic acid molecule is cDNA.

* * * * *